US006255114B1

(12) United States Patent
Lightner et al.

(10) Patent No.: US 6,255,114 B1
(45) Date of Patent: Jul. 3, 2001

(54) STARCH BIOSYNTHETIC ENZYMES

(75) Inventors: Jonathan Edward Lightner, Airville, PA (US); John D. Everard, Wilmington, DE (US)

(73) Assignee: E. I. du Pont de Nemours & Company, Wilmington, DE (US)

(*) Notice: Subject to any disclaimer, the term of this patent is extended or adjusted under 35 U.S.C. 154(b) by 0 days.

(21) Appl. No.: 09/073,297

(22) Filed: May 6, 1998

Related U.S. Application Data

(63) Continuation-in-part of application No. 08/852,615, filed on May 7, 1997, now abandoned.

(51) Int. Cl.[7] .............................. C12N 15/29; C12N 5/04; C12N 15/74; C12N 15/82; C12P 19/04

(52) U.S. Cl. .................. 435/468; 435/69.1; 435/70.1; 435/101; 435/252.3; 435/419; 536/23.6; 800/284

(58) Field of Search .................. 536/23.6; 435/69.1, 435/70.1, 101, 252.3, 419, 468; 800/284, 298

(56) References Cited

U.S. PATENT DOCUMENTS

| | | | |
|---|---|---|---|
| 4,945,050 | 7/1990 | Sanford et al. | 435/172.1 |
| 5,107,065 | 4/1992 | Shewmaker et al. | 800/205 |
| 5,231,020 | 7/1993 | Jorgensen et al. | 435/172.3 |
| 5,561,236 | 10/1996 | Leemans et al. | 435/172.3 |
| 5,646,024 | 7/1997 | Leemans et al. | 435/172.3 |

FOREIGN PATENT DOCUMENTS

| | | |
|---|---|---|
| 0355 528 | 3/1989 | (EP). |
| WO 93/02196 | 2/1993 | (WO). |
| WO 94/04693 | 3/1994 | (WO). |
| WO 95/30005 | 11/1995 | (WO). |
| WO 97/13843 | 4/1997 | (WO). |

OTHER PUBLICATIONS

Newman et al. Plant Physiol. 106: 1241–1255, 1994.*
Benning et al. J. Bacteriol. 174(20): 6479–6487, Nov. 1992.*
Osborne B. I. et al., The Sequence of BAC F7G19 from Arabidopsis Thaliana Chromosome, EMBL Sequence Accession No. AC000106, Jan. 27, 1997, XP002078429.
Takahashi, R. et al., Rice mRNA for WSI76 Protein Induced by Water Stress, Complete CDS, EMBL Sequence Accession No. D26537, Feb. 16, 1994, XP002078430.
Minobe, Y. et al., Rice cDNA, partial sequence (C2674_1A), EMBL Sequence Accession No. D23352, Nov. 28, 1993, XP002078432.
Baysdorfer, C. et al., zEST00935 Maize Leaf, Stratagene #937005 Zea Mays cDNA Clone csuh00935 5' End Similar to Water Stress Induced Protein, EMBL Sequence Accession No. W21647, May 8, 1996, XP002078433.
Baysdorfer, C. et al., zEST00924 Maize Leaf, Stratagene #937005 Zea Mays cDNA Clone csuh 00924 5' End Similar to Water Stress Induced Protein, EMBL Sequence Accession No. W21638, May 8, 1996, XP002078434.
Newman, T. et al., 12767 Lambda–PRL2 Arabidopsis Thaliana cDNA Clone 166L16T7, EMBL Sequence Accession No. R30162, Aug. 9, 1995, XP002078435.
Barbetti, F. et al., The Human Skeletal Muscle Glycogenin Gene: cDNA Tissue Expression and Chromosomal Location, Biochemical And Biophysical Research Communications, vol. 220, 1996, pp. 72–77, XP002078436.
Rounsley, S.D., et al., Arabidopsis Thaliana Chromosome II BAC T08113 Genomic Sequence, Complete Sequence, EMBL Sequence Accession No. AC002337, Jul. 18, 1997, XP002078437.
Federspiel, N.A., et al., Arabidopsis Thaliana Chromosome 1 BAC T14N5 Genomic Sequence, Complete Sequence, EMBL Sequence Accession No. AC004260, Mar. 13, 1998, XP002078438.
Biological Abstracts, vol. 95, 1993, Philadelphia, PA, US; Abstract No. 4626, JOSHI, C.P., et al.: Molecular Cloning and Characterization of a cDNA Encoding a Water Stress Protein (WSP23) from Wheat Roots, XP002078440 and Plant Science, vol. 86, No. 1, 1992, pp. 71–82.
Chu et al., *Sci. Sin. Peking*, 18, 659–668, 1975.
Deblaere et al., *Meth. Enzymol.*, 153, 277–292, 1987.
Barbetti, F. et al., *Diabetologia*, 38, 295, 1995.
Raikhel, N., *Plant Phys.*, 1627–1632, 1992.
Smith, A. et al., *Plant Physiol.*, 107, 673–677, 1995.
Turner, R. and Foster, G. D., *Molecular Biotechnology*, 3, 225, 1995.
Wilson, R. et al., *Nature*, 368, 32–38, 1994.
Fromm et al., *Bio/Technology*, 8, 833–839, 1990.
Walker, C.E., *Cereal Foods World*, 33, 491–494, 1988.
J.D. Hoheisel, et al., Non–Mammalian Genomic Anaysis: A Practical Guide, *Academic Press*, 319–346, 1996.
Lander et al., *Genomics*, 1, 174–181, 1987.
Singh, D.G. et al., *FEBS Letters*, 376, 61–64, 1995.
Lerner, R.A., *Adv. Immunol*, 36, 1, Maniatis, 1984.
Altschul, S.F. et al., *J. Mol. Biol.*, 215, 403–410, 1990.
Jones et al., *Embo J.*, 4, 2411–2418, 1985.
Keegstra, K. *Cell*, 56, 247–253, 1989.
Hizukuri, *Carbohydrate Res.*, 147, 342–347, 1986.
Botstein, D. et al., *Am. J. Hum. Genet.*, 32, 314–331, 1980.
Bernatzky, R. and Tanksley, S.D., *Plant Mol. Biol. Reporter*, 4(1), 37–41, 1986.
Okamuro and Goldberg, *Biochemistry of Plants*, 15, 1–82, 1989.

(List continued on next page.)

*Primary Examiner*—David T. Fox

(57) ABSTRACT

This invention relates to isolated nucleic acid fragments encoding all or a substantial portion of a plant glycogenin or water stress protein. The invention also relates to the construction of chimeric genes encoding all or a portion of a plant glycogenin or water stress protein, in sense or antisense orientation, wherein expression of the chimeric gene results in production of altered levels of a plant glycogenin or water stress protein in a transformed host cell.

9 Claims, 5 Drawing Sheets

OTHER PUBLICATIONS

*Biochemical Journal*, 219(No.2), 345–373, 1984.
Takahashi, R. et al., *Plant Mol. Biol.*, 26(1), 339–352, 1994.
*Nucleic Acids Research*, 13, 3021–3030, 1985, Carnish—Bowden, A.
Odell et al., *Nature*, 313, 810–812, 1985.
De Almeida et al., *Mol. Gen. Genetics*, 218, 78–86, 1989.
Loh et al., *Science*, 243, 217, 1989.
Klein et al., *Nature (London)*, 327, 70–73, 1987.
Preiss, J., *Biochemistry of Plants*, 14, 181–254, 1988.
Ingelbrecht et al., *Plant Cell*, 1, 671–680, 1989.
Gish W, and States, D.J., *Nature Genetics*, 3, 266–272, 1993.
Ohara et al., *PNAS USA*, 85, 5673, 1989.
Frohman et al., *PNAS USA*, 85, 8998, 1988.
Chrispeels, J.J., *Ann. Rev. Plant Phys. Plant Mol. Biol.*, 42, 21–53, 1991.
Lomako et al., *Genomics*, 33(3), 519–522, 1996.
Genbank Accession U44131.
DDBJ: Locus RICWS176, Accession D26537.
Genbank: Locus HSU31525, Accession U31525.
EMBL: Locus CET25E12, Accession Z82052.
Accession 1922956, Locus, ATAC000106, EMBL.

* cited by examiner

```
1922956      IRQSGSTKDMILLHDDSITNISLIGLSLAGWKLRRVERIRSPFSKKR--SYNEWNYSKL  357
D26537       LRRVRSAYPLVVAVLPDVPGEHRRKLVEQGCVVREIQPVYPPESQTQFAMAYYVINYSKL  101
cc3.mn0001.f7 IRQAGSTRDLVILVDDTISDHHRKGLESAGWKVRIIQRIRNPKAERD--AYNEWNYSKF  87

1922956      RVWQVTDYDKLVFIDADFIIVKNIDYLFSYPQLSAAGNNKVLFNSGVMVLEPSACLFEDL  417
D26537       RIWEFVEYERMVYLDADIQVFDNIDHLFDL-----DKGAFYAV-----KDCFCEKT  147
cc3.mn0001.f7 RLWQLTDYDKVIFIDADLLILRNIDFLFALPEITATGNNATLFNSGVMVIEPSNCTFRLL  147

1922956      MLKSFKIGSYNGGDQGFLNEYFVWWHRL----SKRLNTMKYF----GDESRHDKARNL-  468
D26537       WSHTPQ---YDIGYCQQRPDEVAWPERELGPPPLYFNAGMFVHEPGLGTAKDLLDALVV  204
cc3.mn0001.f7 MEHIDEITSYNGGDQGYLNEIFTWWHRI-----PKHMNFLKHFWEGDEEEVKAKKTRLFG  202

1922956      --PENLEGIHYLGLKPWRCYRD-YDCNWDLKTRRVYASESVHARWWKVYDKM--PKKLK  521
D26537       TPPTPFAEQDFLN----MFFREQYK---PIPNVY--NLVLAMLWRHPENVDLDQVKVV  253
cc3.mn0001.f7 ANPPVLYVLHYLGRKPWLCFRD-YDCNWNVEILREFASDVAHARWWKVHNRM--PRKLQ  258

1922956      GYCGLNLKMEKNVEKW-RKMAKLNGFPENHWKIRIKDPRKKNRLSQ  566
D26537       HYCA----AGSKPW-RFTGKEENMNREDIKMLVK--RWWDIYND---ESLDYKEEED  300
cc3.mn0001.f7 SYCLLRSSLKAGLE-WERRQAEKANFTDGHWKRNVTDPRLKTCFEKFCFWESMLWHWGEK  317

1922956      NADEASQPMRTALAEAGAVKYFPAP-SAA  566
D26537                                     328
cc3.mn0001.f7 SKSNSTTTRNSAVPATTTTPAAASLSSS  346
```

STARCH BIOSYNTHETIC ENZYMES

This is a continuation-in-part of application Ser. No. 08/852,615 filed May 7, 1997, now abandoned.

FIELD OF THE INVENTION

This invention is in the field of plant molecular biology. More specifically, this invention pertains to nucleic acid fragments encoding enzymes involved in starch biosynthesis in plants and seeds.

BACKGROUND OF THE INVENTION

Starch is an important component of food, feed, and industrial products. Broadly speaking, it consists of two types of glucan polymers: relatively long chained polymers with few branches known as amylose, and shorter chained but highly branched molecules called amylopectin. Its biosynthesis depends on the complex interaction of multiple enzymes (Smith, A. et al., (1995) *Plant Physio.* 107:673–677; Preiss, J., (1988) *Biochemistry of Plants* 14:181–253). Chief among these are ADP-glucose pyrophosphorylase, which catalyzes the formation of ADP-glucose; a series of starch synthases which use ADP glucose as a substrate for polymer formation using α-1-4 linkages; and several starch branching enzymes, which modify the polymer by transferring segments of polymer to other parts of the polymer using α-1-6 linkages, creating branched structures. However, based on data from starch forming plants such as potato, and corn, it is becoming clear that other enzymes also play a role in the determination of the final structure of starch. In particular, debranching and disproportionating enzymes not only participate in starch degradation, but also in modification of starch structure during its biosynthesis. Different models for this action have been proposed, but all share the concept that such activities, or lack thereof, change the structure of the starch produced.

This is of applied interest because changes in starch structure, such as the relative amounts of amnylose and amylopectin or the degree and length of branching of amylopectin, alter its function in cooking and industrial processes. For example, starch derived from different naturally occurring mutants of corn can be shown on the one hand to differ in structure and correspondingly to differ in functional assays such as Rapid Visco analysis, which measures changes in viscosity as starch is heated and then cooled (Walker, C. E., (1988) *Cereal Foods World* 33:491–494). The interplay of different enzymes to produce different structures, and in turn how different structures correlate with different functionalities, is not yet completely understood. However, it is understood that changing starch structure will result in alteration in starch function which can in turn lead to new applications or reduced processing costs (certain starch functionalities can at present only be attained through expensive chemical modification of the starch).

Glycogen, a non-plant analogue of starch, is synthesized by the concerted actions of glycogen synthase and glycogen branching enzymes in much the same way that starch biosynthesis occurs in plants. Glycogen synthesis requires a primer for the initial action of the glycogen synthase enzyme. This primer function is thought to be provided by self-glucosylating protein called glycogenin in mammals. Inactivation of the two genes that encode this enzyme in yeast has been shown to result in the absence of glycogen. It is evident that a similar primer function may be necessary for starch biosynthesis in plants and the isolation of such a self glucosylating activity has been the subject some study (Singh, D. G. et al., (1995) *FEBS Letters* 376:61–64; World Patent Publication No. WO 94/04693). These reports describe the identification and purification a self-glucosylating protein activity from plants that is structurally unrelated to glycogenin. However, these reports provide no direct evidence that this protein is essential for starch biosynthesis. Lastly, the rice gene WSI76 is a gene induced by short term water stress. Its expression is decreased in response to chilling (Plant Mol Biol 1994 October 26(1): 339–352). WS176 may be a rice glycogenin because its only homology to a functionally characterized protein is to glycogenin.

Alterations in starch fine structure are known to result in changes to the physiochemical properties of the starch. Because starch fine structure results from the concerted action of several starch synthases, starch branching enzymes and starch debranching enzymes, it is reasonable to suppose that manipulating the amount of substrate for these enzymes may impact on the ultimate structure of the starch granule. Further it is clear that attempts to manipulate starch fine structure through altering expression of starch biosynthetic genes may lower the overall production of starch by reducing the amount of substrate, glucan chains, available to prime synthesis. One useful approach to resolve such difficulties would be the overexpression of a primer protein, glycogenin. Finally, manipulating the expression of the glycogenin primer may be used, for example, to alter the total number of granules initiated in corn endosperm. Increasing or decreasing the number of initial primers for synthesis might reasonably be expected to decrease or increase, respectively, the ultimate size of the synthesized granules. Altering granule size may usefully alter starch functionality and or starch.

The role of glycogenin in starch biosynthesis suggests that over-expression or reduction of expression of genes encoding glycogenin in corn, rice or wheat could be used to alter branch chain distribution of the starch produced by these plants. While glycogenin genes and genes encoding peptides with homology to glycogenin have been described from other organisms (Barbetti, F. et al. (1995) *Diabetologia* 38:295; Wilson, R. et al. (1994) *Nature* 368:32–38; Takahashi, R. et al. (1994) *Plant Mol. Biol.* 26(1):339–352), a glycogenin gene has yet to be described for corn, rice or wheat.

SUMMARY OF THE INVENTION

The instant invention relates to isolated nucleic acid fragments encoding corn, rice and wheat glycogenin and water stress proteins. In addition, this invention relates to nucleic acid fragments that are complementary to nucleic acid fragments encoding corn, rice and wheat glycogenin and water stress proteins.

In another embodiment, the instant invention relates chimeric genes encoding a corn, rice and wheat glycogenin and water stress protein or nucleic acid fragments that are complementary to nucleic acid fragments encoding a corn, rice and wheat glycogenin and water stress protein, operably linked to suitable regulatory sequences, wherein expression of the chimeric gene results in production of altered levels of a corn, rice and wheat glycogenin or water stress protein in a transformed host cell.

In a further embodiment, the instant invention concerns a transformed host cell comprising in its genome a chimeric gene encoding corn, rice and wheat glycogenin or water stress protein, operably linked to suitable regulatory sequences, wherein expression of the chimeric gene results in production of altered levels of corn, rice and wheat glycogenin or water stress protein in the transformed host cell. The transformed host cells can be of eukaryotic or prokaryotic origin, and include cells derived from higher plants and microorganisms. The invention also includes transformed plants that arise from transformed host cells of higher plants, and from seeds derived from such transformed plants.

An additional embodiment of the instant invention concerns a method of altering the level of expression of a corn, rice and wheat glycogenin or water stress protein in a transformed host cell comprising: a) transforming a host cell with the chimeric gene encoding a corn, rice and wheat glycogenin or water stress protein, operably linked to suitable regulatory sequences; and b) growing the transformed host cell under conditions that are suitable for expression of the chimeric gene wherein expression of the chimeric gene results in production of altered levels of a corn, rice and wheat glycogenin and water stress protein in the transformed host cell.

An addition embodiment of the instant invention concerns a method for obtaining a nucleic acid fragment encoding all or substantially all of an amino acid sequence encoding a plant glycogenin.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows a comparison of the amino acid sequences of human glycogenin (U44131), a *Caenorhabditis elegans* glycogenin homolog (Z82052) and the instant corn glycogenin enzyme (cc3. mn0001.f7).

FIG. 2 shows a comparison of the amino acid sequences of the instant corn glycogenin enzyme (cc3. mn0001.f7) and two related plant sequences: a conceptual translation of a portion of a genomic clone from *Arabidopsis thaliana* (1922956) with homology to glycogenin, and a rice (*Oryza sativa*) protein induced by water stress (D26537).

Figure 3:
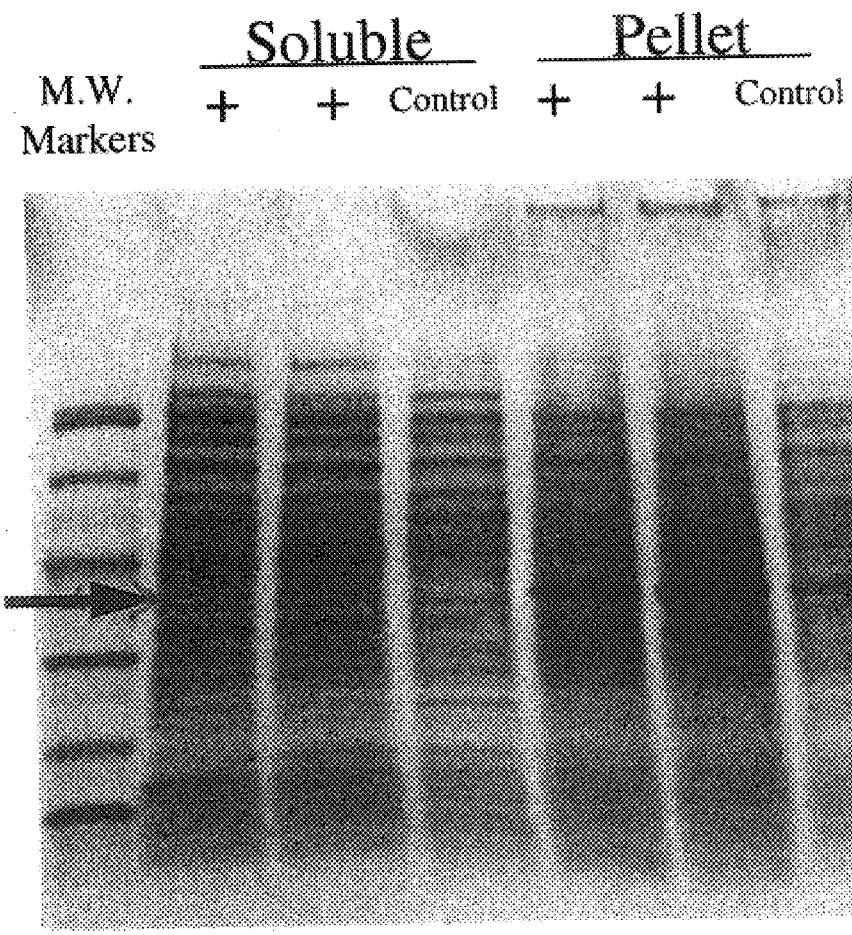

FIG. 3 is a digitized image of a stained SDS-PAGE gel demonstrating expression of the instant corn glycogenin in *E. coli*. "Soluble" indicates that the analyzed samples were obtained from the soluble fraction of the cell extract. "Pellet" indicates that the analyzed samples were obtained from the insoluble fraction of the cell extract. A "+" sign indicates that the analyzed samples were extracted from *E. coli* transformants harboring an expression vector comprising the PCR generated EST cc3.mn0001.f7 insert. "Control" indicates that the analyzed samples were extracted from *E. coli* transfornants harboring an empty pET24d expression vector.

SEQ ID NO:1 is the nucleotide sequence comprising a portion of the cDNA insert in clone cc3.mn0001.f7 encoding a corn glycogenin.

SEQ ID NO:2 is the deduced amino acid sequence of a corn glycogenin derived from the nucleotide sequence of SEQ ID NO:1.

SEQ ID NO:3 is the amino acid sequence encoding the human glycogenin having GenBank Accession No. U44131.

SEQ ID NO:4 is the amino acid sequence encoding the *Caenorhabditis elegans* glycogenin homolog having EMBL Accession No. Z82052.

SEQ ID NO:5 is the amino acid sequence encoding a conceptual translation of a portion of a genomic clone from *Arabidopsis thaliana* having GenBank Accession No. 1922956.

SEQ ID NO:6 is the amino acid sequence encoding the rice water stress-induced protein having DDJB Accession No. D26537.

SEQ ID NO:7 is a PCR primer used in the construction of a plasmid vector suitable for expression of the instant corn glycogenin in *E. coli*.

SEQ ID NO:8 is a PCR primers used in the construction of a plasmid vector suitable for expression of the instant corn glycogenin in *E. coli*.

SEQ ID NO:9 is the nucleotide sequence comprising a portion of the cDNA insert in clone cr1n.pk0033. g10 encoding a corn glycogenin.

SEQ ID NO:10 is the deduced amino acid sequence of a corn glycogenin derived from the nucleotide sequence of SEQ ID NO:9.

SEQ ID NO:11 is the nucleotide sequence of a portion of the cDNA insert in clone cta1n.pk0013.e6 encoding a corn glycogenin.

SEQ ID NO:12 is the deduced amino acid sequence of a corn glycogenin derived from the nucleotide sequence of SEQ ID NO:11.

SEQ ID NO:13 is the nucleotide sequence comprising a portion of the cDNA insert in clone r10n.pk0027.f11 encoding a rice water stress protein.

SEQ ID NO:14 is the deduced amino acid sequence of a water stress protein derived from the nucleotide sequence of SEQ ID NO:13.

SEQ ID NO:15 is the nucleotide sequence comprising a portion of the cDNA insert in clone rr1.pk0070.e9 encoding a rice glycogenin.

SEQ ID NO:16 is the deduced amino acid sequence of a rice glycogenin derived from the nucleotide sequence of SEQ ID NO:15.

SEQ ID NO:17 is the nucleotide sequence a contig assembled from the cDNA inserts in clones wre1n.pk0137.d9 and wre1n.pk0107.h10 encoding a wheat glycogenin.

SEQ ID NO:18 is the deduced amino acid sequence of a glycogenin derived from the nucleotide sequence of SEQ ID NO:17.

SEQ ID NO:19 is the nucleotide sequence comprising a portion of the cDNA insert in clone wl1m1.pk0014.g10 encoding a wheat glycogenin.

SEQ ID NO:20 is the deduced amino acid sequence of a glycogenin derived from the nucleotide sequence of SEQ ID NO:19.

SEQ ID NO:21 is the nucleotide sequence comprising a portion of the cDNA insert in clone wl1n.pk0035.h9 encoding a wheat glycogenin.

SEQ ID NO:22 is the deduced amino acid sequence of a glycogenin derived from the nucleotide sequence of SEQ ID NO:21.

SEQ ID NO:23 is the nucleotide sequence comprising a portion of the cDNA insert in clone wl1n.pk0148.f10 encoding a wheat glycogenin.

SEQ ID NO:24 is the deduced amino acid sequence of a wheat glycogenin derived from the nucleotide sequence of SEQ ID NO:23.

SEQ ID NO:25 is the nucleotide sequence of a portion of the cDNA insert in clone wle1n.pk0056.b2 encoding a wheat water stress.

SEQ ID NO:26 is the deduced amino acid sequence of a water stress protein derived from the nucleotide sequence of SEQ ID NO:25.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the corn, rice and wheat glycogenin and water stress proteins as set forth in SEQ ID NOs:2, 10, 12, 14, 16, 18, 20, 22, 24 and 26. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propetides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, N. (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050).

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Maniatis").

This invention relates to corn, rice and wheat cDNAs with homology to glycogenin from mammals and other organisms and rice and wheat cDNAs with homology to water stress proteins from rice. Glycogenin and water stress protein genes from other plants can now be identified by comparison of random cDNA sequences to the corn, rice and wheat glycogenin and water stress protein sequences provided herein.

The nucleic acid fragments of the instant invention may be used to isolate cDNAs and genes encoding homologous glycogenins and water stress proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, other glycogenin or water stress genes, either as cDNAs or genomic DNAs, could be isolated directly by using all or a portion of the instant glycogenin or water stress genes as a DNA hybridization probes to screen libraries from any desired plant employing methodology well known to those skilled in the art. Specific oligonucleotide probes based upon the instant glycogenin or water stress sequences can be designed and synthesized by methods known in the art (Maniatis). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequence. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous glycogenin or water stress protein genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding plant glycogenin. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate fill-length cDNA clones of interest (Lerner, R. A. (1984) *Adv. Immunol.* 36:1; Maniatis).

The nucleic acid fragments of the instant invention may be used to create transgenic plants in which an instant glycogenin or water stress protein is present at higher or lower levels than normal or in cell types or developmental stages in which it is not normally found. This may have the effect of altering starch structure in those cells.

Overexpression of a corn, rice and wheat glycogenin and water stress protein may be accomplished by first constructing a chimeric gene in which a corn, rice and wheat glycogenin or water stress protein coding region is operably linked to a promoter capable of directing expression of a gene in the desired tissues at the desired stage of development. For reasons of convenience, the chimeric gene may comprise a promoter sequence and translation leader sequence derived from the same gene. 3' Non-coding sequences encoding transcription termination signals must also be provided. The instant chimeric genes may also comprise one or more introns in order to facilitate gene expression.

A plasmid vector comprising the instant chimeric gene is then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mnRNA expression, Western analysis of protein expression, or phenotypic analysis.

For some applications it may be useful to direct the glycogenin or water stress protein to different cellular compartments, or to facilitate its secretion from the cell. It is thus envisioned that the chimeric gene described above may be further supplemented by altering the coding sequence to encode a glycogenin or water stress protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future. It may also be desirable to reduce or eliminate expression of the glycogenin or water stress protein gene in plants for some applications. In order to accomplish this, a chimeric gene designed for co-suppression of glycogenin can be constructed by linking the glycogenin gene or gene fragment to a plant promoter sequences. Alternatively, a chimeric gene designed to express antisense RNA for all or part of the glycogenin gene can be constructed by linking the glycogenin gene or gene fragment in reverse orientation to a plant promoter sequences. Either the co-suppression or antisense chimeric gene could be introduced into plants via transformation wherein expression of the endogenous glycogenin gene is reduced or eliminated.

Corn, rice and wheat glycogenin or water stress proteins produced in heterologous host cells, particularly in the cells of microbial hosts, can be used to prepare antibodies to the protein by methods well known to those skilled in the art. The antibodies are useful for detecting corn, rice and wheat glycogenin or water stress proteins in situ in cells or in vitro in cell extracts. Preferred heterologous host cells for production of a corn, rice or wheat glycogenin and water stress protein are microbial hosts. Microbial expression systems and expression vectors containing regulatory sequences that direct high level expression of foreign proteins are well known to those skilled in the art. Any of these could be used to construct chimeric genes for production of a corn, rice and wheat glycogenin or water stress proteins. These chimeric genes could then be introduced into appropriate microorganisms via transformation to provide high level expression of a corn, rice and wheat glycogenin and water stress proteins. An example of a vector for high level expression of a corn, rice and wheat glycogenin or water stress protein in a bacterial host is provided (Example 4).

All or a portion of the nucleic acid fragments of the instant invention may also be used as probes for genetically and physically mapping the genes that they are a part of, and as markers for traits linked to expression of a corn, rice and wheat glycogenin or water stress protein. Such information may be useful in plant breeding in order to develop lines with desired starch phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant MoL. Biol. Reporter* 4(1): 37–41. Numerous publications describe genetic mapping of specific cDNA clones using the methodology outlined above or variations thereof For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (13allinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the corn, rice and wheat glycogenin or water stress protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a corn, rice and wheat glycogenin or water stress protein can be identified and obtained. This mutant plant can then be used to determine or confirm the natural function of the corn, rice and wheat glycogenin or water stress protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of Corn, Rice and Wheat cDNA Libryrs; Isolation and Sequencing of cDNA Clones A cDNA library representing mRNAs from corn embryogenic callus derived from corn embryos obtained from *Zea mays* LH132 corn plants (library desigantion: cc3) was prepared. The cDNA library was prepared in a Uni-ZA™ XR vector according to the manufacturer's protocol (Stratagene Cloning Systems, La Jolla, Calif.). Conversion of the Uni-ZAP™ XR library into a plasmid library was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted corn cDNA sequences. Amplified insert DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer. cDNA libraries representing mRNAs from various other corn, rice and wheat tissues were also prepared as describe above. The characteristics of these libraries are described below.

TABLE 1 cDNA Libraries from Corn, Rice and Wheat

| Library | Tissue | Clone |
|---------|--------|-------|
| cr1n | Corn Root From 7 Day Seedlings Grown In Light* | cr1n.pk0033.g10 |
| cta1n | Corn Tassel* | cta1n.pk0027.e11 |
| r10n | Rice 15 Day Leaf* | r10n.pk0027.f11 |
| rr1 | Rice Root Two Week Old Developing Seedling | rr1.pk0070.e9 |
| wre1n | Wheat Root From 7 Day Old Etiolated Seedling* | wre1n.pk0137.d9 |
|  |  | wre1n.pk0107.h10 |
| wl1n | Wheat Leaf Obtained From 7 Day Old Seedling* | wl1n.pk0035.h9 |
|  |  | wl1n.pk0148.f10 |
| wle1n | Wheat Leaf From 7 Day Old Etiolated Seedling* | wle1n.pk0056.b2 |
| wlm1 | Wheat Seedling 1 Hour After Inoculation With *Erysiphe graminis* | wlm1.pk0014.g10 |

*These libraries were normalized essentially as described in U.S. Pat. No. 5,482,845

Example 2

Identification and Characterization of cDNA Clones

ESTs encoding glycogenin were identified by conducting a BLAST (Basic Local Alignment Search Tool; Altschul, S. F., et al., (1990) *J. Mol. Biol.* 215:403–410; see also www.ncbi.nlm.nih.gov/BLAST/) search for similarity to sequences contained in the GenBank database. The cDNA sequences obtained in Example 1 was analyzed for similarity to all publicly available DNA sequences contained in the GenBank Database using the BLASTN algorithm provided by the National Center for Biotechnology Information (NCBI). The DNA sequences were translated in all reading frames and compared for similarity to all publicly available protein sequences contained in the GeneBank Database using the BLASIX algorithm (Gish, W. and States, D. J. (1993) *Nature Genetics* 3:266–272) provided by the NCBI.

The BLASTX search using clone cc3.mn0001.f7 revealed similarity of the protein encoded by the cDNA to human glycogenin (GenBank Accession No. U31525; logP=23.47). The sequence of the entire cDNA insert in clone cc3.mn0001.f7 was then determined and is depicted in SEQ ID NO:1. The corresponding amino acid sequence of the corn glycogenin protein is shown in SEQ ID NO:2. The amino acid sequence was then analyzed for similarity to all publically available sequences using the BLASTP algorithm provided by the NCBI. The BLASTP search using the sequence depicted in SEQ ID NO:2 revealed significant homology to human glycogenin (GenBank Accession No. U44131; logP=19.62) and a *Caenorhabditis elegans* glycogenin homolog (EMBL Accession No. Z82052; logP=21.60). The BLASTP search also revealed homology of the instant corn EST to two plant peptide sequences: a conceptual translation of a portion of a genomic clone from *Arabidopsis thaliana* (GenBank Accession No. 1922956; logP=116.77) with homology to glycogenin, and a rice (*Oryza sativa*) protein induced by water stress (DDJB Accession No. D26537; logP=16.89). The amino acid sequence of the instant corn glycogenin shows approximately 19.2, 20.3, 43.1 and 16.8% sequence similarity (calculated using Clustal Method and the PAM250 Weight Table (DNASTAR Inc., Madison, Wis.) to the human, *C. elegans*, Arabidopsis and rice sequences, respectively. Sequence alignments and BLAST scores and probabilities indicate that the instant nucleic acid fragment encodes a corn glycogenin enzyme.

Example 3

Characterization of cDNA Clones Encoding Other Glycogenins or Water Stress Proteins The BLASTX search using the EST sequences from several clones revealed similarity of the proteins encoded by the cDNAs to glycogenins or water stress proteins from different organisms. The BLAST results for each of these ESTs are shown in Table 2:

TABLE 2

BLAST Results for Clones Encoding Polypeptides Homologous to Glycogenin or Water Stress Proteins

| Clone | Protein | Organism | GenBank Accession No. | Blast pLog score |
|---|---|---|---|---|
| cr1n.pk0033.g10 | Glycogenin | *Rhodobacter sphaeroides* | M89780 | 10.57 |
| r10n.pk0027.f11 | Water Stress Protein | *Oryza sativa* | D26537 | 39.36 |
| rr1.pk0070.e9 | Water Stress Protein | *Caenorhabditis elegans* | U64599 | 17.59 |
| wl1n.pk0035.h9 | Glycogenin | *Caenorhabditis elegans* | U64599 | 6.24 |
| wl1n.pk0148.f10 | Glycogenin | *Caenorhabditis elegans* | U64599 | 13.85 |
| wle1n.pk0056.b2 | Glycogenin | *Caenorhabditis elegans* | U64599 | 6.72 |
| wlm1.pk0014.g10 | Water Stress Protein | *Oryza sativa* | D26537 | 22.51 |

BLAST scores and probabilities indicate that the instant nucleic acid fragments encode portions of glycogenin or water stress proteins. These sequences represent additional, heretofore unrecognized corn sequences encoding glycogenin. In addition, the wheat clones described above represent the first wheat sequences encoding a glycogenin or water stress protein. Clones r10n.pk0027.f11 and rr1.pk0070.e9 appear to encode proteins that belong to the water stress protein gene family but have not been previously identified in rice. This conclusion is based on the fact that r10n.pk0027.f11 and rr1.pk0070.e9 bear little or no homology to known rice water stress proteins genes as evidenced by their low pLog scores.

Two other clones, ct1n.pk0013.e6 and wre1n.pk0137.d9, were identified as encoding glycogenin by their homology to cc3.mm0001.f7. When compared to cc3.mm0001.f7 by BLAST, they had pLog values of 50.69 for cta1n.pk0013.e6 and 41.30 for wre1n.pk0107.h10. An additional wheat clone, wre1n.pk0107.h10, was identified by BLAST homology to wre1n.pk0137.d9. When compared, wre1n.pk0107.h10 and wre1n.pk0137.d9 were found have an overlapping region of nearly 100% identity. Using this homology it was possible to align these clones and assemble a contig (a contig is an assemblage of overlapping nucleic acid sequences to form one contiguous nucleotide sequence). The individual sequences were assembled into a unique contiguous nucleotide sequence encoding a unique wheat glycogenin protein. The SEQ ID NOs for each the above clones and the wheat glycogenin contig are shown in Table 3:

TABLE 3

Sequence Identification Numbers for Clones Encoding Polypeptides Homologous to Glycogenin or Water Stress Proteins

| | SEQ ID NOs. | |
|---|---|---|
| Clone | Nucleotide Sequence | Amino Acid Sequence |
| cr1n.pk0033.g10 | 9 | 10 |
| cta1n.pk0013.e6 | 11 | 12 |
| r10n.pk0027.f11 | 13 | 14 |
| rr1.pk0070.e9 | 15 | 16 |
| Contig composed of: wre1n.pk0137.d9 wre1n.pk0107.h10 | 17 | 18 |
| wlm1.pk0014.g10 | 19 | 20 |
| wl1n.pk0035.h9 | 21 | 22 |
| wl1n.pk0148.f10 | 23 | 24 |
| wle1n.pk0056.b2 | 25 | 26 |

Example 4

Expression of Chimeric Genes in Plant Cells

A chimeric gene comprising a corn, rice or wheat glycogenin or water stress protein cDNA in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone comprising a corn, rice or wheat glycogenin or water stress protein using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 uL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 0.001% w/v gelatin, 200 mM dGTP, 200 mM DATP, 200 mM dTTP, 200 mM dCTP and 0.025 unit Amplitaq™ DNA polymerase. Reactions are carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 12301 Parklawn Drive, Rockville, Md. 20852), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, the corn, rice or wheat glycogenin or water stress protein cDNA fragment, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *BiolTechnology* 8:833–839).

Starch extracted from single seeds obtained from plants transformed with the chimeric gene can then be analyzed. Seeds can be steeped in a solution containing 1.0% lactic acid and 0.3% sodium metabisulfite, pH 3.8, held at 52° C. for 22–24 h. Seeds are then drained, rinsed and homogenized individually in 8–9 mL of a solution of 100 mM NaCl. Five mL of toluene are added to each tube and vigorously shaken twice for 6 minutes using a paint mixer, and allowed to settle for 30 minutes. Two mL of 100 mM NaCl is sprayed onto the solution, allowed to settle for 30 minutes, and the protein-toluene layer is aspirated off. The toluene wash step is repeated. Twelve mL water is added and shaken in a paint shaker for 45 seconds. This solution is centrifuged for 10 minutes and the water is removed. The water wash is repeated, followed by a final wash with 12 mL of acetone. After shaking and centrifugation steps, the acetone is drained and allowed to evaporate for 1 h. Starch extracts are incubated in a 40° C. oven overnight.

Extracted starches can be enzymatically debranched as follows. Seven mg of each starch sample is added to a screw cap test tube containing 1.1 mL of water. The tubes are heated to 120° C. for 30 minutes and then placed in a water bath at 45° C. Debranching solution can be prepared by diluting 50 µL of isoamylase ($5 \times 10^6$ units/mL; Sigma) per mL of 50 mM NaOAc buffer, pH 4.5. Forty µL of debranching solution is added to each starch sample, and the samples are incubated in a water bath at 45° C. for 3 h. The debranching reaction is stopped by heating samples to 110° C. for 5 minutes. Debranched starch samples can then be lyophilized and redissolved in DMSO.

One hundred µL of each debranched starch can then be analyzed by gel permeation chromotography (GPC). One hundred µL of each debranched starch is injected and chromatographed by passage through two GPC columns (Mixed Bed-C; Polymer Labs) arranged in series. Chromatography is performed at 100° C. and samples are eluted with DMSO at a flow rate of 1.0 mL/min. Chromatographic samples are collected at 25 minute intervals. A refractive index detector (Waters) can be used for detection, and data can be collected and stored with the aid of a computer running Chemstation Software (version A.02.05; Hewlett-Packard).

Retention times of collected samples may then be compared to retention times of pullulan standards (380K, 100K, 23.7K, 5.8K, 728 and 180 mw). The proportion of the total starch is determined for twenty-four ranges of degree of polymerization (DP) spanning both the amylose and amylopectin portions of the chromatogram. The percentage area in appropriate DP ranges is used to determine values for A & B1, B2, B3 and B4+ chains of the amylopectin portion of the chromatogram. The proportion of the total area above DP 150 is used to determine amylose content.

Amylopectin is typically described by its distribution of branch chains in the molecule. The amylopectin molecule is comprised of alternating crystalline and amorphous regions. The crystalline region is where many of the branch points ($\alpha$-1,6 linkages) occur, while the amorphous region is an area of little to no branching and few branch chains. The type of chain may be designated as A or B. A chains are unbranched and span a single crystalline region. B1 chains also span a single crystalline region but are branched. B2, B3 and B4+ chains are branched and span 2, 3 and 4 or more crystalline regions, respectively (Hizukuri (1986) *Carbohydrate Res.* 147:342–347). The relative area under the amylopectin portion of the chromatograms can be used to determine the area percentage of the A & B1, B2, B3 and B4+ chains.

Starches derived from plants transformed with the chimeric gene can also be tested for functionality by techniques well known to those skilled in the art. For example, starch can be extracted from dry mature kernels from transformed plants. Fifteen g of kernels are weighed into a 50 mL Erlenmeyer flask and steeped in 50 mL of steep solution (same as above) for 18 h at 52° C. The kernels are drained and rinsed with water. The kernels are then homogenized using a 20 mm Polytron probe (Kinematica GmbH; Kriens-Luzem, Switzerland) in 50 mL of cold 50 mM NaCl. The homogenate is filtered through a 72 micron mesh screen. The filtrate is brought up to a total volume of 400 mL with 50 mM NaCl and an equal volume of toluene is added. The mixture is stirred with a magnetic stir bar for 1 h at sufficient speed to completely emulsify the two phases. The emulsion is allowed to separate overnight in a covered beaker. The upper toluene layer is aspirated from the beaker and discarded. The starch slurry remaining in the bottom of the beaker is resuspended, poured into a 250 mL centrifuge bottle and centrifuged 15 minutes at 25,000 RCF. The supernatant is discarded and the starch is washed sequentially with water and acetone by shaking and centrifuging as above. After the acetone wash and centrifugation the acetone is decanted and the starch allowed to dry overnight in a fume hood at room temperature.

A Rapid Visco Analyzer (Newport Scientific; Sydney, Australia) with high sensitivity option and Thermocline software can then be used for pasting curve analysis. For each line, 1.50 g of starch is weighed into the sample cup and 25 mL of phosphate/citrate buffer (pH 6.50) containing 1% NaCl was added. Pasting curve analysis can be performed using the following temperature profile: idle temperature 50° C., hold at 50° C. for 0.5 minutes, linear heating to 95° C. for 2.5 minutes, linear cooling to 50° C. over 4 minutes, hold at 50° C. for four minutes.

Results of the Rapid Visco Analyzer pasting analysis may demonstrate that the starch produced by lines transformed with the chimeric gene differ in its pasting properties both from normal dent starch. This result may demonstrate that the alteration of starch fine structure produced by altering expression of a corn, rice or wheat glycogenin or water stress protein can create a starch of novel functionality.

The size of the individual starch granules is an important component of milling yield, as well as a contributing factor in starch functionality. Because decreases of increases in the amount of glycogenin primer may reduce or increase, respectively, the number of starch granules initiated, the resulting granules may be expected to be altered in size relative to normal maize starch granules. Starch extracted from individual kernels can be subjected to Particle Size Analysis (PSA). 7.5 mg of starch is dispersed in dispersing solution comprising 0.2% Triton X-100 in water (v/v) and sonicated for 15 minutes. The particle size of the dispersion is then measured using a PSA2010 Particle Size Analyzer (Galai Production Ltd.) equipped with a BCM-1 Cell Module. Particle size measurements are made according to the manufacturer's instructions. Changes in granule size may indicate altered starch functionality or millability.

Example 5

Expression of Corn Glycogenin in *E. coli*

For expression in *E. coli*, the EST clone cc3.mn0001.f7 was placed into the pET24d T7 expression vector (Novagen) by PCR amplification using primers depicted in SEQ ID NO:7 and SEQ ID NO:8. For PCR, Vent™ DNA polymerase (New England Biolabs) was used with an additional 2 µL of 100 mM magnesium sulfate added to each 100 µL reaction. The 5' primer has the sequence shown in SEQ ID NO:7 and consists of bases 26 to 46 of SEQ ID NO:1, additional bases 5'-catgccatgg-3' added to encode an Nco I site in the primer and four additional 5' bases to enhance the restriction enzyme recognintion of the encoded Nco I site. The 3' primer has the sequence shown in SEQ ID NO:8 and consists of the reverse complement of bases 625 to 646 in pBluescript-SK (Stratagene). The PCR reaction comprised for 25 cycles using the following protocol:55° C. annealing temperature and 1.5 minute extension time. A product of about 1400 base pairs was obtained and purified using Wizard™ PCR purification kit (Perkin-Elmer). Four micrograms of the PCR product was digested for 18 hours at 37° C. with NcoI and XhoI. The digested DNA was deproteinated by extraction with an equal volume of 1:1 phenol:chloroform, extraction of the upper layer of the phenol:chloroform separation with 1 volume of chloroform, and precipitation with ethanol. One microgram of digested PCR product was then ligated with 200 ng of pET24d T7 expression vector (Novogen) that had also been previously digested with NcoI and XhoI. The ligation mixture was used to transform electrocompetent BL21 (DE3) (Novagen) *E. coli* cells and transformants were selected by growth on plates containing 50 mg/L kanamycin. Eighteen single colonies from the transformation plate were chosen to inoculate 3 mL cultures of 2×YT media containing 50 mg/L kanamycin in preparation for plasmid purification. Insertion of the PCR product in the expression vector was determined by restriction enzyme analysis using NcoI and XhoI.

Three kanamycin resistant clones were chosen for inoculation of overnight cultures. Two of the clones contained the PCR generated EST cc3.mn0001.f7 insert, while the third clone was an empty pET24d vector to act as a control. The overnight cultures which were grown at 30° C. in 2×YT media containing 50 mg/L kanamycin were diluted two fold with fresh media, allowed to re-grow for 1 h, then induced by adding isopropyl-thiogalactoside to 1mM fimal concentration. Following a 3 h induction period, cells were harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads were added and the mixture was sonicated 3 times for about 5 seconds each time with a microprobe sonicator. The mixture was centrifuged and the protein concentration of the supernatant and pellet were determined. One μg of protein from the soluble fraction and pellet of each clonal culture was separated by SDS-polyacrylamide gel electrophoresis. The cultures contiaing the corn glycogenin cDNA insert produced an additional protein band of about 42 kilodaltons in mass predominately in the pellet fraction with a small percentage in the soluble fraction (FIG. 3).

What is claimed is:

1. An isolated polynucleotide comprising:
   (a) a first nucleotide sequence encoding a first glycogenin comprising 346 amino acids, wherein, the first nucleotide sequence and the nucleotide sequence of SEQ ID NO:1 have at least 80% identity based on the Clustal alignment method,
   b) a second nucleotide sequence encoding a second glycognin comprising 71 amino acids, wherein the second nucleotide sequence and the nucleotide sequence of SEQ ID NO:9 have at least 80% identity based on the Clustal alignment method,
   (c) a third nucleotide sequence encoding a third glycogenin comprising 93 amino acids, wherein the third nucleotide sequence and the nucleotide sequence of SEQ ID NO:11 have at least 80% identity based on the Clustal alignment method, or
   (d) the complement of the first, second, or third nucleotide sequence.

2. The polynucleotide of claim 1, wherein the first nucleotide sequence and the nucleotide sequence of SEQ ID NO:1 have at least 90% identity based on the Clustal alignment method, wherein the second nucleotide sequence and the nucleotide sequence of SEQ ID NO:9 have at least 90% identity based on the Clustal alignment method, and wherein the third nucleotide sequence and the nucleotide sequence of SEQ ID NO;11 have at least 90% identity based on the Clustal alignment method.

3. The polynucleotide of claim 1, wherein the first nucleotide sequence and the nucleotide sequence of SEQ ID NO:1 have at least 95% identity based on the Clustal alignment method, wherein the second nucleotide sequence and the nucleotide sequence of SEQ ID NO:9 have at least 95% identity based on the Clustal alignment method, and wherein the third nucleotide sequence and the nucleotide sequence of SEQ ID NO:11 have at least 95% identity based on the Clustal alignment method.

4. The polynucleotide of claim 1, wherein the first nucleotide sequence comprises the nucleotide sequence of SEQ ID NO:9, wherein the second nucleotide sequence comprises the nucleotide sequence of SEQ ID NO:1, and wherein tube third nucleotide sequence comprises the nucleotide sequence of SEQ ID NO:11.

5. The polynucleotide of claim 1, wherein the first glycogenin comprises the amino acid sequence of SEQ ID NO:2, wherein the second glycogenin comprises the amino acid sequence of SEQ ID NO:10, and wherein the third glycogenin comprises the amino acid sequence of SEQ ID NO:12.

6. A chimeric gene comprising the polynucleotide of claim 1 operably linked to a regulatory sequence.

7. A method for transforming a cell comprising transforming a cell with the polynucleotide of claim 1.

8. A transformed host cell comprising the chimeric gene of claim 6.

9. An isolated polynucleotide comprising a nucleotide sequence comprised by the polynucleotide of claim 1, wherein the nucleotide sequence contains at least 30 nucleotides.

* * * * *

UNITED STATES PATENT AND TRADEMARK OFFICE
CERTIFICATE OF CORRECTION

PATENT NO.    : 6,255,114 B1                                                    Page 1 of 1
DATED         : July 3, 2001
INVENTOR(S)   : John D. Everard and Jonathan E. Lightner It is certified that error appears in the above-identified patent and that said Letters Patent is hereby corrected as shown below:

<u>Column 52,</u>
Line 9, delete "SEQ ID NO:9" and insert -- SEQ ID NO:1 --.
Line 11, delete "SEQ ID NO:1" and insert -- SEQ ID NO:9 --.
Line 12, delete "tube" and insert -- the --.

Signed and Sealed this

Fourth Day of May, 2004

JON W. DUDAS
*Acting Director of the United States Patent and Trademark Office*

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
        (A) LENGTH: 1333 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1039

(xi) SEQUENCE DESCRIPTION: SEQ ID NO: 1:

```
G GAA TTC GGC ACG AGA CGC AGA GAA GCA TAT GCT ACA ATA CTG CAT       46
  Glu Phe Gly Thr Arg Arg Arg Glu Ala Tyr Ala Thr Ile Leu His
   1               5                  10                  15

TCA GCA AGT GAA TAT GTT TGC GGC GCG ATC ACG GCA GCT CAA AGC ATT     94
Ser Ala Ser Glu Tyr Val Cys Gly Ala Ile Thr Ala Ala Gln Ser Ile
                 20                  25                  30

CGT CAG GCA GGA TCA ACA AGA GAC CTA GTT ATT CTC GTC GAC GAC ACC    142
Arg Gln Ala Gly Ser Thr Arg Asp Leu Val Ile Leu Val Asp Asp Thr
             35                  40                  45

ATA AGT GAC CAC CAC CGC AAG GGG CTG GAA TCT GCG GGG TGG AAG GTC    190
Ile Ser Asp His His Arg Lys Gly Leu Glu Ser Ala Gly Trp Lys Val
         50                  55                  60

AGG ATA ATA CAG AGG ATC CGG AAC CCC AAA GCC GAG CGC GAC GCC TAC    238
Arg Ile Ile Gln Arg Ile Arg Asn Pro Lys Ala Glu Arg Asp Ala Tyr
     65                  70                  75

AAC GAG TGG AAC TAC AGC AAA TTC CGG CTG TGG CAG CTC ACG GAT TAC    286
Asn Glu Trp Asn Tyr Ser Lys Phe Arg Leu Trp Gln Leu Thr Asp Tyr
 80                  85                  90                  95

GAC AAG GTC ATC TTC ATC GAC GCG GAT CTC CTC ATC CTG AGG AAC ATC    334
Asp Lys Val Ile Phe Ile Asp Ala Asp Leu Leu Ile Leu Arg Asn Ile
                100                 105                 110

GAT TTC CTG TTC GCG CTG CCG GAG ATC ACG GCG ACG GGG AAC AAC GCG    382
Asp Phe Leu Phe Ala Leu Pro Glu Ile Thr Ala Thr Gly Asn Asn Ala
            115                 120                 125

ACG CTC TTC AAC TCG GGA GTG ATG GTC ATC GAG CCT TCG AAC TGC ACG    430
Thr Leu Phe Asn Ser Gly Val Met Val Ile Glu Pro Ser Asn Cys Thr
        130                 135                 140

TTC CGG CTA CTG ATG GAG CAC ATC GAC GAG ATA ACG TCG TAC AAC GGC    478
Phe Arg Leu Leu Met Glu His Ile Asp Glu Ile Thr Ser Tyr Asn Gly
    145                 150                 155

GGG GAC CAG GGG TAC CTG AAC GAG ATA TTC ACG TGG TGG CAC CGG ATC    526
Gly Asp Gln Gly Tyr Leu Asn Glu Ile Phe Thr Trp Trp His Arg Ile
160                 165                 170                 175

CCG AAG CAC ATG AAC TTC CTG AAG CAT TTC TGG GAG GGC GAC GAG GAG    574
Pro Lys His Met Asn Phe Leu Lys His Phe Trp Glu Gly Asp Glu Glu
                180                 185                 190
```

```
GAG GTG AAG GCG AAG AAG ACC CGG CTG TTC GGC GCG AAC CCG CCG GTC        622
Glu Val Lys Ala Lys Lys Thr Arg Leu Phe Gly Ala Asn Pro Pro Val
            195                 200                 205

CTC TAC GTG CTC CAC TAC CTG GGG AGG AAG CCG TGG CTG TGC TTC CGG        670
Leu Tyr Val Leu His Tyr Leu Gly Arg Lys Pro Trp Leu Cys Phe Arg
        210                 215                 220

GAC TAC GAC TGC AAC TGG AAC GTG GAG ATC CTG CGG GAG TTC GCG AGC        718
Asp Tyr Asp Cys Asn Trp Asn Val Glu Ile Leu Arg Glu Phe Ala Ser
        225                 230                 235

GAC GTC GCG CAC GCC CGC TGG TGG AAG GTG CAC AAC CGG ATG CCC AGG        766
Asp Val Ala His Ala Arg Trp Trp Lys Val His Asn Arg Met Pro Arg
240                 245                 250                 255

AAG CTC CAG AGC TAC TGC CTT CTG AGG TCG AGC CTG AAG GCC GGG CTG        814
Lys Leu Gln Ser Tyr Cys Leu Leu Arg Ser Ser Leu Lys Ala Gly Leu
            260                 265                 270

GAG TGG GAG CGG CGG CAG GCC GAG AAG GCG AAC TTC ACG GAC GGG CAT        862
Glu Trp Glu Arg Arg Gln Ala Glu Lys Ala Asn Phe Thr Asp Gly His
            275                 280                 285

TGG AAG CGG AAC GTA ACG GAC CCG AGG CTG AAG ACC TGC TTC GAG AAG        910
Trp Lys Arg Asn Val Thr Asp Pro Arg Leu Lys Thr Cys Phe Glu Lys
        290                 295                 300

TTC TGC TTC TGG GAG AGC ATG CTG TGG CAC TGG GGC GAG AAG AGC AAG        958
Phe Cys Phe Trp Glu Ser Met Leu Trp His Trp Gly Glu Lys Ser Lys
        305                 310                 315

AGC AAC TCG ACG ACG ACG CGG AAC AGC GCC GTG CCG GCA ACA ACA ACG       1006
Ser Asn Ser Thr Thr Thr Arg Asn Ser Ala Val Pro Ala Thr Thr Thr
320                 325                 330                 335

ACA ACG CCT GCT GCT GCG AGC CTG TCG AGC TCG TGAGACTTGT AGATAGCTCT     1059
Thr Thr Pro Ala Ala Ala Ser Leu Ser Ser Ser
            340                 345

GTCTGCCGAG AGTAGTATAC CAGTACCAGA TACAGAACTT CTGAAGCTCC ATACATACAT     1119

AGCGACAGCT CTGTAAAGGT AGCTATGTAG GCCTTTTCCT TCCCCGAATG ACTATATACC     1179

TTCGTCTTCG TTCGCCGTCA CAGCTGCAGG CAGCTCCCTC CCTCCCGCTG GTTTCCGATG     1239

GTTAACAATT CTTTTGTTTT TGCCAATAAT TCATCAGTAT AGGATGTCAG GCTATGTTGC     1299

CTCAATTCCC AGTGGCAAAA AAAAAAAAAA AAAA                                 1333

(2) INFORMATION FOR SEQ ID NO: 2:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO: 2:

Glu Phe Gly Thr Arg Arg Arg Glu Ala Tyr Ala Thr Ile Leu His Ser
1               5                   10                  15

Ala Ser Glu Tyr Val Cys Gly Ala Ile Thr Ala Ala Gln Ser Ile Arg
            20                  25                  30

Gln Ala Gly Ser Thr Arg Asp Leu Val Ile Leu Val Asp Asp Thr Ile
        35                  40                  45

Ser Asp His His Arg Lys Gly Leu Glu Ser Ala Gly Trp Lys Val Arg
    50                  55                  60

Ile Ile Gln Arg Ile Arg Asn Pro Lys Ala Glu Arg Asp Ala Tyr Asn
65                  70                  75                  80

Glu Trp Asn Tyr Ser Lys Phe Arg Leu Trp Gln Leu Thr Asp Tyr Asp
            85                  90                  95
```

```
Lys Val Ile Phe Ile Asp Ala Asp Leu Ile Leu Arg Asn Ile Asp
            100                 105                 110
Phe Leu Phe Ala Leu Pro Glu Ile Thr Ala Thr Gly Asn Asn Ala Thr
        115                 120                 125
Leu Phe Asn Ser Gly Val Met Val Ile Glu Pro Ser Asn Cys Thr Phe
    130                 135                 140
Arg Leu Leu Met Glu His Ile Asp Glu Ile Thr Ser Tyr Asn Gly Gly
145                 150                 155                 160
Asp Gln Gly Tyr Leu Asn Glu Ile Phe Thr Trp Trp His Arg Ile Pro
                165                 170                 175
Lys His Met Asn Phe Leu Lys His Phe Trp Glu Gly Asp Glu Glu Glu
            180                 185                 190
Val Lys Ala Lys Lys Thr Arg Leu Phe Gly Ala Asn Pro Pro Val Leu
        195                 200                 205
Tyr Val Leu His Tyr Leu Gly Arg Lys Pro Trp Leu Cys Phe Arg Asp
    210                 215                 220
Tyr Asp Cys Asn Trp Asn Val Glu Ile Leu Arg Glu Phe Ala Ser Asp
225                 230                 235                 240
Val Ala His Ala Arg Trp Trp Lys Val His Asn Arg Met Pro Arg Lys
                245                 250                 255
Leu Gln Ser Tyr Cys Leu Leu Arg Ser Ser Leu Lys Ala Gly Leu Glu
            260                 265                 270
Trp Glu Arg Arg Gln Ala Glu Lys Ala Asn Phe Thr Asp Gly His Trp
        275                 280                 285
Lys Arg Asn Val Thr Asp Pro Arg Leu Lys Thr Cys Phe Glu Lys Phe
    290                 295                 300
Cys Phe Trp Glu Ser Met Leu Trp His Trp Gly Glu Lys Ser Lys Ser
305                 310                 315                 320
Asn Ser Thr Thr Thr Arg Asn Ser Ala Val Pro Ala Thr Thr Thr Thr
                325                 330                 335
Thr Pro Ala Ala Ala Ser Leu Ser Ser Ser
                340                 345

(2) INFORMATION FOR SEQ ID NO: 3:

(i) SEQUENCE CHARACTERISTICS:
        (A) LENGTH: 333 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 3:

Met Thr Asp Gln Ala Phe Val Thr Leu Thr Thr Asn Asp Ala Tyr Ala
1               5                   10                  15
Lys Gly Ala Leu Val Leu Gly Ser Ser Leu Lys Gln His Arg Thr Thr
            20                  25                  30
Arg Arg Leu Val Val Leu Ala Thr Pro Gln Val Ser Asp Ser Met Arg
        35                  40                  45
Lys Val Leu Glu Thr Val Phe Asp Glu Val Ile Met Val Asp Val Leu
    50                  55                  60
Asp Ser Gly Asp Ser Ala His Leu Thr Leu Met Lys Arg Pro Glu Leu
65                  70                  75                  80
Gly Val Thr Leu Thr Lys Leu His Cys Trp Ser Leu Thr Gln Tyr Ser
                85                  90                  95
```

```
Lys Cys Val Phe Met Asp Ala Asp Thr Leu Val Leu Ala Asn Ile Asp
                100                 105                 110

Asp Leu Phe Asp Arg Glu Glu Leu Ser Ala Ala Pro Asp Pro Gly Trp
            115                 120                 125

Pro Asp Cys Phe Asn Ser Gly Val Phe Val Tyr Gln Pro Ser Val Glu
        130                 135                 140

Thr Tyr Asn Gln Leu Leu His Leu Ala Ser Glu Gln Gly Ser Phe Asp
145                 150                 155                 160

Gly Gly Asp Gln Gly Ile Leu Asn Thr Phe Phe Ser Ser Trp Ala Thr
                165                 170                 175

Thr Asp Ile Arg Lys His Leu Pro Phe Ile Tyr Asn Leu Ser Ser Ile
            180                 185                 190

Ser Ile Tyr Ser Tyr Leu Pro Ala Phe Lys Val Phe Gly Ala Ser Ala
        195                 200                 205

Lys Val Val His Phe Leu Gly Arg Val Lys Pro Trp Asn Tyr Thr Tyr
210                 215                 220

Asp Pro Lys Thr Lys Ser Val Lys Ser Glu Ala His Asp Pro Asn Met
225                 230                 235                 240

Thr His Pro Glu Phe Leu Ile Leu Trp Trp Asn Ile Phe Thr Thr Asn
                245                 250                 255

Val Leu Pro Leu Leu Gln Gln Phe Gly Leu Val Lys Asp Thr Cys Ser
            260                 265                 270

Tyr Val Asn Val Glu Asp Val Ser Gly Ala Ile Ser His Leu Ser Leu
        275                 280                 285

Gly Glu Ile Pro Ala Met Ala Gln Pro Phe Val Ser Ser Glu Glu Arg
    290                 295                 300

Lys Glu Arg Trp Glu Gln Gly Gln Ala Asp Tyr Met Gly Ala Asp Ser
305                 310                 315                 320

Phe Asp Asn Ile Lys Arg Lys Leu Asp Thr Tyr Leu Gln
                325                 330

(2) INFORMATION FOR SEQ ID NO: 4:

(i) SEQUENCE CHARACTERISTICS:
        (A) LENGTH: 300 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 4:

Met Thr Glu Ala Trp Ile Thr Leu Ala Thr Asn Asp Arg Tyr Ala Gln
1               5                   10                  15

Gly Ala Leu Thr Leu Leu Asn Ser Leu His Ala Ser Gly Thr Thr Arg
            20                  25                  30

Arg Ile His Cys Leu Ile Thr Asn Glu Ile Ser Asn Ser Val Arg Glu
        35                  40                  45

Lys Leu Val Asn Lys Phe Asp Glu Val Thr Val Val Asp Ile Phe Asn
    50                  55                  60

Ser Asn Asp Ser Glu Asn Leu Ser Leu Ile Gly Arg Pro Asp Leu Gly
65                  70                  75                  80

Val Thr Phe Thr Lys Phe His Cys Trp Arg Leu Thr Gln Tyr Ser Lys
                85                  90                  95

Ala Val Phe Leu Asp Ala Asp Thr Met Ile Ile Arg Asn Ser Asp Glu
                100                 105                 110
```

```
Leu Phe Glu Arg Pro Asp Phe Ser Ala Ala Ala Asp Ile Gly Trp Pro
        115                 120                 125

Asp Met Phe Asn Ser Gly Val Phe Val Phe Thr Pro Ser Leu Thr Val
130                 135                 140

Tyr Arg Ala Leu Leu Ser Leu Ala Thr Ser Ser Gly Ser Phe Asp Gly
145                 150                 155                 160

Gly Asp Gln Gly Leu Leu Asn Glu Tyr Phe Ser Asn Trp Arg Asp Leu
                165                 170                 175

Pro Ser Ala His Arg Leu Pro Phe Ile Tyr Asn Met Thr Ala Gly Glu
            180                 185                 190

Phe Tyr Ser Tyr Pro Ala Ala Tyr Arg Lys Tyr Gly Ala Gln Thr Lys
        195                 200                 205

Ile Val His Phe Ile Gly Ala Gln Lys Pro Trp Asn Ser Pro Pro Ser
    210                 215                 220

Asp Ser Gly Leu His Lys Asn Glu His Tyr Gln Gln Trp His Ser Phe
225                 230                 235                 240

Ser Leu Gln Ser Ser Ser Ser Glu Ala Pro Ala Ala Pro Lys Val
                245                 250                 255

Glu Asp Asp Ser Glu Lys Gln Arg Ile Ala Trp Glu Ala Gly His Pro
                260                 265                 270

Asp Tyr Leu Gly Lys Asp Ala Phe Lys Asn Ile Gln Lys Ala Leu Asp
            275                 280                 285

Glu Ser Met Ala Ala Val Lys Pro Pro Ala Lys Pro
290                 295                 300

(2) INFORMATION FOR SEQ ID NO: 5:

(i) SEQUENCE CHARACTERISTICS:
        (A) LENGTH: 566 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 5:

Met Gly Ala Lys Ser Lys Ser Ser Thr Arg Phe Phe Met Phe Tyr
1               5                   10                  15

Leu Ile Leu Ile Ser Leu Ser Phe Leu Gly Leu Leu Asn Phe Lys
            20                  25                  30

Pro Leu Phe Leu Leu Asn Pro Met Ile Ala Ser Pro Ser Ile Val Glu
        35                  40                  45

Ile Arg Tyr Ser Leu Pro Glu Pro Val Lys Arg Thr Pro Ile Trp Leu
    50                  55                  60

Arg Leu Ile Arg Asn Tyr Leu Pro Asp Glu Lys Lys Ile Arg Val Gly
65                  70                  75                  80

Leu Leu Asn Ile Ala Glu Asn Glu Arg Glu Ser Tyr Glu Ala Ser Gly
                85                  90                  95

Thr Ser Ile Leu Glu Asn Val His Val Ser Leu Asp Pro Leu Pro Asn
                100                 105                 110

Asn Leu Thr Trp Thr Ser Leu Phe Pro Val Trp Ile Asp Glu Asp His
            115                 120                 125

Thr Trp His Ile Pro Ser Cys Pro Glu Val Pro Leu Pro Lys Met Glu
        130                 135                 140

Gly Ser Glu Ala Asp Val Asp Val Val Val Lys Val Pro Cys Asp
145                 150                 155                 160
```

-continued

```
Gly Phe Ser Glu Lys Arg Gly Leu Arg Asp Val Phe Arg Leu Gln Val
                165                 170                 175
Asn Leu Ala Ala Ala Asn Leu Val Val Glu Ser Gly Arg Arg Asn Val
            180                 185                 190
Asp Arg Thr Val Tyr Val Val Phe Ile Gly Ser Cys Gly Pro Met His
        195                 200                 205
Glu Ile Phe Arg Cys Asp Glu Arg Val Lys Arg Val Gly Asp Tyr Trp
    210                 215                 220
Val Tyr Arg Pro Asp Leu Thr Arg Leu Lys Gln Lys Leu Leu Met Pro
225                 230                 235                 240
Pro Gly Ser Cys Gln Ile Ala Pro Leu Gly Gln Gly Glu Ala Trp Ile
            245                 250                 255
Gln Asp Lys Asn Arg Asn Leu Thr Ser Glu Lys Thr Thr Leu Ser Ser
            260                 265                 270
Phe Thr Ala Gln Arg Val Ala Tyr Val Thr Leu Leu His Ser Ser Glu
        275                 280                 285
Val Tyr Val Cys Gly Ala Ile Ala Leu Ala Gln Ser Ile Arg Gln Ser
    290                 295                 300
Gly Ser Thr Lys Asp Met Ile Leu Leu His Asp Asp Ser Ile Thr Asn
305                 310                 315                 320
Ile Ser Leu Ile Gly Leu Ser Leu Ala Gly Trp Lys Leu Arg Arg Val
            325                 330                 335
Glu Arg Ile Arg Ser Pro Phe Ser Lys Lys Arg Ser Tyr Asn Glu Trp
            340                 345                 350
Asn Tyr Ser Lys Leu Arg Val Trp Gln Val Thr Asp Tyr Asp Lys Leu
        355                 360                 365
Val Phe Ile Asp Ala Asp Phe Ile Val Lys Asn Ile Asp Tyr Leu
    370                 375                 380
Phe Ser Tyr Pro Gln Leu Ser Ala Ala Gly Asn Asn Lys Val Leu Phe
385                 390                 395                 400
Asn Ser Gly Val Met Val Leu Glu Pro Ser Ala Cys Leu Phe Glu Asp
            405                 410                 415
Leu Met Leu Lys Ser Phe Lys Ile Gly Ser Tyr Asn Gly Gly Asp Gln
            420                 425                 430
Gly Phe Leu Asn Glu Tyr Phe Val Trp Trp His Arg Leu Ser Lys Arg
        435                 440                 445
Leu Asn Thr Met Lys Tyr Phe Gly Asp Glu Ser Arg His Asp Lys Ala
    450                 455                 460
Arg Asn Leu Pro Glu Asn Leu Glu Gly Ile His Tyr Leu Gly Leu Lys
465                 470                 475                 480
Pro Trp Arg Cys Tyr Arg Asp Tyr Asp Cys Asn Trp Asp Leu Lys Thr
            485                 490                 495
Arg Arg Val Tyr Ala Ser Glu Ser Val His Ala Arg Trp Trp Lys Val
        500                 505                 510
Tyr Asp Lys Met Pro Lys Lys Leu Lys Gly Tyr Cys Gly Leu Asn Leu
    515                 520                 525
Lys Met Glu Lys Asn Val Glu Lys Trp Arg Lys Met Ala Lys Leu Asn
530                 535                 540
Gly Phe Pro Glu Asn His Trp Lys Ile Arg Ile Lys Asp Pro Arg Lys
545                 550                 555                 560
Lys Asn Arg Leu Ser Gln
            565
```

(2) INFORMATION FOR SEQ ID NO: 6:

(i) SEQUENCE CHARACTERISTICS:
        (A) LENGTH: 328 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 6:

```
Met Met Gly Pro Asn Val Ser Ser Glu Lys Lys Ala Leu Ala Ala Ala
 1               5                  10                  15

Lys Arg Arg Ala Tyr Val Thr Phe Leu Ala Gly Asp Gly Asp Tyr Trp
                20                  25                  30

Lys Gly Val Val Gly Leu Ala Lys Gly Leu Arg Arg Val Arg Ser Ala
                35                  40                  45

Tyr Pro Leu Val Val Ala Val Leu Pro Asp Val Pro Gly Glu His Arg
 50                  55                  60

Arg Lys Leu Val Glu Gln Gly Cys Val Val Arg Glu Ile Gln Pro Val
 65                  70                  75                  80

Tyr Pro Pro Glu Ser Gln Thr Gln Phe Ala Met Ala Tyr Tyr Val Ile
                85                  90                  95

Asn Tyr Ser Lys Leu Arg Ile Trp Glu Phe Val Glu Tyr Glu Arg Met
                100                 105                 110

Val Tyr Leu Asp Ala Asp Ile Gln Val Phe Asp Asn Ile Asp His Leu
                115                 120                 125

Phe Asp Leu Asp Lys Gly Ala Phe Tyr Ala Val Lys Asp Cys Phe Cys
130                 135                 140

Glu Lys Thr Trp Ser His Thr Pro Gln Tyr Asp Ile Gly Tyr Cys Gln
145                 150                 155                 160

Gln Arg Pro Asp Glu Val Ala Trp Pro Glu Arg Glu Leu Gly Pro Pro
                165                 170                 175

Pro Pro Leu Tyr Phe Asn Ala Gly Met Phe Val His Glu Pro Gly Leu
                180                 185                 190

Gly Thr Ala Lys Asp Leu Leu Asp Ala Leu Val Val Thr Pro Pro Thr
                195                 200                 205

Pro Phe Ala Glu Gln Asp Phe Leu Asn Met Phe Phe Arg Glu Gln Tyr
                210                 215                 220

Lys Pro Ile Pro Asn Val Tyr Asn Leu Val Leu Ala Met Leu Trp Arg
225                 230                 235                 240

His Pro Glu Asn Val Asp Leu Asp Gln Val Lys Val Val His Tyr Cys
                245                 250                 255

Ala Ala Gly Ser Lys Pro Trp Arg Phe Thr Gly Lys Glu Glu Asn Met
                260                 265                 270

Asn Arg Glu Asp Ile Lys Met Leu Val Lys Arg Trp Trp Asp Ile Tyr
                275                 280                 285

Asn Asp Glu Ser Leu Asp Tyr Lys Glu Glu Asp Asn Ala Asp Glu
                290                 295                 300

Ala Ser Gln Pro Met Arg Thr Ala Leu Ala Glu Ala Gly Ala Val Lys
305                 310                 315                 320

Tyr Phe Pro Ala Pro Ser Ala Ala
                325
```

(2) INFORMATION FOR SEQ ID NO: 7:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 7:

CATGCCATGG CATATGCTAC AATACTGCAT                              30

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GTAATACGAC TCACTATAGG GC                                      22

(2) INFORMATION FOR SEQ ID NO: 9:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cr1n.pk0033.g10

(xi) SEQUENCE DESCRIPTION: SEQ ID NO: 9:

GTTGTACAGT CCTGACTCCA AGGCGTTGAG GGAAAAGCTC AGGCTTCCAG TCGGGTCCTG    60

TGAGCTTGCC GTTCCACTCA AAGCCAAATC GAGGCTTTTC TCGGTAGATC GACGAAGAGA   120

AGCGTACGCA NCGATACTGC ATTCAGCGAG CGAATACGTC TGCGGCGCAA TCTCGGCAGC   180

GCAAAGCATC CGCCAGGCAG GATCCACCAG GGACCTGGTC ATCCTTGTGG ACGAGACCAT   240

AAGCGACCAC CACCGGAGAG GCTTGGAGGC GGCGGGGTGG AAGGTCAGAG TGATCCAGAG   300

GATCAGGAAC CCCAAGGCGG ACGCGACGCT ACAACGAGTG GAACTACAGC AAGTTCAGGC   360

TGTGGCAGCT CACCGACTAC GACAAGGTCA TCTTCATAGA CGCCGACCTC CTCATCCTGA   420

GGAACGTCGA CTTCCTGTTC GCCATGCCGG AGATTCGCC                         459

(2) INFORMATION FOR SEQ ID NO: 10:

(i) SEQUENCE CHARACTERISTICS:
        (A) LENGTH: 71 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: cr1n.pk0033.g10

(xi) SEQUENCE DESCRIPTION: SEQ ID NO: 10:

Arg Arg Arg Glu Ala Tyr Ala Xaa Ile Leu His Ser Ala Ser Glu Tyr
1               5                  10                  15

Val Cys Gly Ala Ile Ser Ala Ala Gln Ser Ile Arg Gln Ala Gly Ser

```
                    20                  25                  30
Thr Arg Asp Leu Val Ile Leu Val Asp Glu Thr Ile Ser Asp His His
            35                  40                  45
Arg Arg Gly Leu Glu Ala Ala Gly Trp Lys Val Arg Val Ile Gln Arg
    50                  55                  60
Ile Arg Asn Pro Lys Ala Asp
65                  70
```

(2) INFORMATION FOR SEQ ID NO: 11:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cta1n.pk0013.e6

(xi) SEQUENCE DESCRIPTION: SEQ ID NO: 11:

```
CTCTTCTCTT GCAAGGACCT AGTGAAACGT GAAGGCAATG CTTGGATGTA CAAACCTGAC    60
GTGAAGGCTC TAAAGGAGAA GCTCAGGTTG CCTGTCGGTT CCTGTGAGCT TGCTGTTCCA   120
CTCAACGCAA AAGCACGACT CTACACGGTA GACAGACGCA GAGAAGCATA TGCTACAATA   180
CTGCATTCAG CAAGTGAATA TGTTTGCGGT GCGATAACAG CAGCTCAAAG CATTCGTCAA   240
GCAGGATCAA CAAGGGACCT TGTTATTCTT GTTGATGACA CCATTAGTGA CCACCACCGC   300
AAGGGGCTGG AATCTGCTGG GTGGAAGGTT AGAATAATAC AGAGGATCCG GAATCCCAAA   360
GCGGAACGTG ATGCCTACAA TGAATGGAAC TACAGCAAAT TCCGGCTGTG GCAGCTTACA   420
GATTACGACA AGGNATTTTA TTGATGCTGA TCGCTCATCC TGAGGAAATT GATTCNTGTT   480
TGCATGCCGG AAATCANCGC AACTGGGAAA NAT                                513
```

(2) INFORMATION FOR SEQ ID NO: 12:

(i) SEQUENCE CHARACTERISTICS:
        (A) LENGTH: 93 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: cta1n.pk0013.e6

(xi) SEQUENCE DESCRIPTION: SEQ ID NO: 12:

```
Arg Arg Arg Glu Ala Tyr Ala Thr Ile Leu His Ser Ala Ser Glu Tyr
1               5                   10                  15
Val Cys Gly Ala Ile Thr Ala Ala Gln Ser Ile Arg Gln Ala Gly Ser
                20                  25                  30
Thr Arg Asp Leu Val Ile Leu Val Asp Asp Thr Ile Ser Asp His His
            35                  40                  45
Arg Lys Gly Leu Glu Ser Ala Gly Trp Lys Val Arg Ile Ile Gln Arg
    50                  55                  60
Ile Arg Asn Pro Lys Ala Glu Arg Asp Ala Tyr Asn Glu Trp Asn Tyr
65                  70                  75                  80
Ser Lys Phe Arg Leu Trp Gln Leu Thr Asp Tyr Asp Lys
                85                  90
```

(2) INFORMATION FOR SEQ ID NO: 13:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: rl0n.pk0027.f11

(xi) SEQUENCE DESCRIPTION: SEQ ID NO: 13:

```
CTTACACACC AATCCATTGA AGCAAATTAA CATTTCTCTT GCAAATTTCG ATCTAGCTAG      60
ATCATTTGCA AAGCTTGTTT GTTGATCGAT CGATGATGGG GCCGAACGTG TCGTCGGAGA     120
AGAAGGCGTT GGCGGCGGCG AAGAGGAGGG CGTACGTGAC GTTCCTGGCC GGCGACGGCG     180
ACTACTGGAA GGGCGTCGTG GGCTCGCCA AGGGGCTCCG CCGCGTCCGC TCGGCGTACC      240
CGCTGGTGGT CGCCGTGCTC CCGGACGTCC CCGGCGAGCA CCGGCGGAAC TGGTCGAGCA     300
GGGGTGCGTG GTCCGGGAGA TTCAGCCGGT GTACCCGCCG AANAGCCAGA CGAATTCGCA     360
ATGGCTAATT ACGGGTTAAA CTACTCGANG CTCGNATCGG AATTCCTGAA TACCAACGAT     420
GG                                                                    422
```

(2) INFORMATION FOR SEQ ID NO: 14:

(i) SEQUENCE CHARACTERISTICS:
        (A) LENGTH: 71 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: rl0n.pk0027.f11

(xi) SEQUENCE DESCRIPTION: SEQ ID NO: 14:

```
Met Met Gly Pro Asn Val Ser Ser Glu Lys Lys Ala Leu Ala Ala Ala
1               5                   10                  15
Lys Arg Arg Ala Tyr Val Thr Phe Leu Ala Gly Asp Gly Asp Tyr Trp
            20                  25                  30
Lys Gly Val Val Gly Leu Ala Lys Gly Leu Arg Arg Val Arg Ser Ala
        35                  40                  45
Tyr Pro Leu Val Val Ala Val Leu Pro Asp Val Pro Gly Glu His Arg
    50                  55                  60
Arg Lys Leu Val Glu Gln Gly
65                  70
```

(2) INFORMATION FOR SEQ ID NO: 15:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: rr1.pk0070.e9

(xi) SEQUENCE DESCRIPTION: SEQ ID NO: 15:

-continued

```
CCACCGAAAA GGATTGGAGG CTGCAGGCTG GAAGGTGAGG GTTATCCAAA GAATCAGGAA      60

TCCAAAAGCT GAGCGCGATG CTTACAATGA GTGGAACTAC AGCAAGTTCA GGTTGTGGCA     120

GCTGACCGAC TATGACAAGA TCATATTCAT AGATGCTGAT CTCCTTATCC TGAGGAACGT     180

CGACTTCCTG TTCGCGATGC CAGAGATCAC CGCAACTGGC AACAATGCGA CACTCTTCAA     240

CTCCGGTGTG ATGGTCATCG AGCCGTCAAA CTGCACATTC CAGCTACTGA TGGATCACAT     300

CAATGAGATA ACATCGTACA ACGGCGGTGA CCAAGGATAT CTGAATGAGA TATTCACATG     360

GTGGCACCGC ATCCCCAAGC ACATGAACTT CTTGAAGCNT CTGGGAAGGG GGACGACGAT     420

TCTGCAAAGG CGAAGAAGAC TGAGCTGTTT GGCGCAGACC CGCCTATCCT CTATGTCCTC     480

CACTACCTGG GCATGAAGCC ATGGCTGTGC T                                    511
```

(2) INFORMATION FOR SEQ ID NO: 16:

(i) SEQUENCE CHARACTERISTICS:
        (A) LENGTH: 132 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: rr1.pk0070.e9

(xi) SEQUENCE DESCRIPTION: SEQ ID NO: 16:

```
His Arg Lys Gly Leu Glu Ala Ala Gly Trp Lys Val Arg Val Ile Gln
1               5                   10                  15

Arg Ile Arg Asn Pro Lys Ala Glu Arg Asp Ala Tyr Asn Glu Trp Asn
            20                  25                  30

Tyr Ser Lys Phe Arg Leu Trp Gln Leu Thr Asp Tyr Asp Lys Ile Ile
        35                  40                  45

Phe Ile Asp Ala Asp Leu Leu Ile Leu Arg Asn Val Asp Phe Leu Phe
    50                  55                  60

Ala Met Pro Glu Ile Thr Ala Thr Gly Asn Asn Ala Thr Leu Phe Asn
65                  70                  75                  80

Ser Gly Val Met Val Ile Glu Pro Ser Asn Cys Thr Phe Gln Leu Leu
                85                  90                  95

Met Asp His Ile Asn Glu Ile Thr Ser Tyr Asn Gly Gly Asp Gln Gly
            100                 105                 110

Tyr Leu Asn Glu Ile Phe Thr Trp Trp His Arg Ile Pro Lys His Met
        115                 120                 125

Asn Phe Leu Lys
    130
```

(2) INFORMATION FOR SEQ ID NO: 17:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
AAGCGACGTC GCGCACAGCC GGTGGTGGAA GACGCACGAC AAGATGCCCC GGAAGCTCCA      60

GTCCTACTGC CTTCTGAGGA CAAGGCAGAA GGCTGGGCTG GAGTGGGACC GGAGGCAGGC     120

GGAGAAGGCG AACCTGGAGG ATGGGCATTG GCGGCGGAAC ATCACCGATC CGAGGCTCAA     180
```

```
GACCTGCTTC GAGAAGTTTT GCTTCTGGGA GAGCATGCTG TGGCACTGGG GCGAGGCGAA    240

GAACCAGACG AAGAGCATCC CCGCGCCGGC GACGCCTGCG ACGATGAGCT TGTCAAGTTC    300

GTGAGCTGTG TAGATAGCCC GAGATATTAT ACAGAAGAAA AGTTCATCAT ATGTATACAC    360

CGTACCTGCA TAGCAGCAGT TTGTATANGT ACTATGCTTA NGGCTTCCCC ACACAAATAC    420

AACCTCCTCC TGTTGCCNCC TCCTGGGTGC ANTCTCANCC TGGNACCTTG GGTGGTGGCA    480

ACATCCTTTG GGTTGGGTTA ACTAATAGTA TCGTGTAGTA ATCCTTACNA ANAACGGATT    540

TTCCA                                                                545
```

(2) INFORMATION FOR SEQ ID NO: 18:

(i) SEQUENCE CHARACTERISTICS:
        (A) LENGTH: 78 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 18:

```
Ser Asp Val Ala His Ser Arg Trp Trp Lys Thr His Asp Lys Met Pro
1               5                   10                  15
Arg Lys Leu Gln Ser Tyr Cys Leu Leu Arg Thr Arg Gln Lys Ala Gly
            20                  25                  30
Leu Glu Trp Asp Arg Arg Gln Ala Glu Lys Ala Asn Leu Glu Asp Gly
        35                  40                  45
His Trp Arg Arg Asn Ile Thr Asp Pro Arg Leu Lys Thr Cys Phe Glu
    50                  55                  60
Lys Phe Cys Phe Trp Glu Ser Met Leu Trp His Trp Gly Glu
65                  70                  75
```

(2) INFORMATION FOR SEQ ID NO: 19:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wlm1.pk0014.g10

(xi) SEQUENCE DESCRIPTION: SEQ ID NO: 19:

```
GTCTGGCCGG AGCGCGACCT CGGCGTGCCC CCGCCGCCGC TCTANTTCAA CGCCGGCATG     60

TTCGTGCACG AGCCCAGCAT GGNCANCGCC AAGGCCCTGC TCGACAACTT GTCGTCACCG    120

ACCCCACCCC CTTCGCCGAG CAGGACTTTC TTAACATGTT CTTCAGGGAC GTGTACAAGC    180

CCATCCCGCC GGTGTACAAC CTCGTGCTCG CCATGCTCTG GAGGAACCCG AGAAATCCAG    240

TCCACAAGTC AAAGGTCTCA ATACTGGCGC GGTTCNAACC NTGGGGGTNA NCCGGNAAGG    300

AGGCAAANAT GGANAGGNNC AATTCAAAAT NTGGCAAAA TTGGGGGGAA TTNGAANAAC    360

AAGGCTAAAT AAACCTNCCC CAACAAGGCC CAACCTTNTT TNGCCTCCCA GGNTTCCTTA    420

TTCTTCCGGG GCATACTGNT ATCTCNCNCC ATTAGGTATN TCCAAAAAAC TTNGN         475
```

(2) INFORMATION FOR SEQ ID NO: 20:

(i) SEQUENCE CHARACTERISTICS:

(A) LENGTH: 43 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: wlm1.pk0014.g10

(xi) SEQUENCE DESCRIPTION: SEQ ID NO: 20:

```
Leu Val Val Thr Asp Pro Thr Pro Phe Ala Glu Gln Asp Phe Leu Asn
 1               5                  10                  15

Met Phe Phe Arg Asp Val Tyr Lys Pro Ile Pro Val Tyr Asn Leu
             20                  25                  30

Val Leu Ala Met Leu Trp Arg Asn Pro Arg Asn
             35                  40
```

(2) INFORMATION FOR SEQ ID NO: 21:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wln.pk0035.h9

(xi) SEQUENCE DESCRIPTION: SEQ ID NO: 21:

```
CATANTCATA NATGCTGATC TGCNCANCCT GANGAACATT GATTTCCNGT TTACAANGCT      60

GGAAATCAGT GCAACCGGCA ACANTGCANC ACTCTTCAAC TCTGGTGTCA TGGTTATCGA     120

TCCTTCAAAC TGCACATTCC AGCTGTTANT GAATCACATC AACNAGATCA CATCTTACAA     180

TGGTGGNGAT CAGGGATACT TGAACGAAAT ATTCACATGG TGGCATCGGA TTCCAAANCA     240

CATGAATTCC TGAAGCATTC TGGGAGGGTG ACGAAA                               276
```

(2) INFORMATION FOR SEQ ID NO: 22:

(i) SEQUENCE CHARACTERISTICS:
        (A) LENGTH: 82 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: wln.pk0035.h9

(xi) SEQUENCE DESCRIPTION: SEQ ID NO: 22:

```
Ile Xaa Ile Xaa Ala Asp Leu Xaa Xaa Leu Xaa Asn Ile Asp Phe Xaa
 1               5                  10                  15

Phe Thr Xaa Leu Glu Ile Ser Ala Thr Gly Asn Xaa Ala Xaa Leu Phe
             20                  25                  30

Asn Ser Gly Val Met Val Ile Asp Pro Ser Asn Cys Thr Phe Gln Leu
             35                  40                  45

Leu Xaa Asn His Ile Asn Xaa Ile Thr Ser Tyr Asn Gly Gly Asp Gln
             50                  55                  60

Gly Tyr Leu Asn Glu Ile Phe Thr Trp Trp His Arg Ile Pro Xaa His
65                   70                  75                  80

Met Asn
```

(2) INFORMATION FOR SEQ ID NO: 23:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wl1n.pk0148.f10

(xi) SEQUENCE DESCRIPTION: SEQ ID NO: 23:

```
GGACGCCCCG GCGGATCAAG CGCATCCGCA ACCCGCGCGC GGCGCGGGGC ACCTACAACG      60

AGTACAACTA CAGCAAGTTC CGGCTGTGGC AGCTGGCCGA CTACGACCGC GTGGTGTTCG     120

TGGACGCCGA CATCCTGGTG CTGCGCGACC TGGACGCGCT GTTCGCGTTC CCGCAGCTGG     180

CGGCGGTGGG CAACGACGGC TCGCTCTTCA ACTCGGGCGT GATGGTGATC GAACCGTCGG     240

CGTGCACGTT CGACGCGCTC ATGCGGGGGC GCCGGACCGT CCGCTCGTAC AACGGCGGCG     300

ACCAGGGGTT CCTCAACGAG GTGTTCGTGT GGTGGCACCG CCTGCCGCGC CGGGTCAACT     360

ACCTCAAGAA CTTCTGGGCC AACACCACGG GGGAGCGCGC GCTCAAGGAG AGGCTGTTCC     420

GGGCGGACCC GCCCGANGTC TGGTCCGTCA ACTANCTGGG GATGAAGCAT GGACGGCTAC     480

ANGGACTACG ACTGCAACTG GAACTGGCGG ACAAAAGGTG NCGCAACGAC AAGCCACCCC     540

GCTGGTGGAA GTGACACAAA TGGGGACANA TCCC                                574
```

(2) INFORMATION FOR SEQ ID NO: 24:

(i) SEQUENCE CHARACTERISTICS:
        (A) LENGTH: 120 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: wl1n.pko148.f10

(xi) SEQUENCE DESCRIPTION: SEQ ID NO: 24:

```
Arg Arg Ile Lys Arg Ile Arg Asn Pro Arg Ala Ala Arg Gly Thr Tyr
 1               5                  10                  15

Asn Glu Tyr Asn Tyr Ser Lys Phe Arg Leu Trp Gln Leu Ala Asp Tyr
                20                  25                  30

Asp Arg Val Val Phe Val Asp Ala Asp Ile Leu Val Leu Arg Asp Leu
            35                  40                  45

Asp Ala Leu Phe Ala Phe Pro Gln Leu Ala Ala Val Gly Asn Asp Gly
        50                  55                  60

Ser Leu Phe Asn Ser Gly Val Met Val Ile Glu Pro Ser Ala Cys Thr
65                  70                  75                  80

Phe Asp Ala Leu Met Arg Gly Arg Arg Thr Val Arg Ser Tyr Asn Gly
                85                  90                  95

Gly Asp Gln Gly Phe Leu Asn Glu Val Phe Val Trp Trp His Arg Leu
            100                 105                 110

Pro Arg Arg Val Asn Tyr Leu Lys
        115                 120
```

(2) INFORMATION FOR SEQ ID NO: 25:

(i) SEQUENCE CHARACTERISTICS:
        (A) LENGTH: 598 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wle1n.pk0056.b2

(xi) SEQUENCE DESCRIPTION: SEQ ID NO: 25:

GAGGAATGTG GACTTCCTGT TCGCAATGCC AGAGATCACC GCGACCGGCA ACAACGCAAC       60

CCTCTTCAAC TCCGGCGTCA TGGTGATCGA GCCCTCAAAC TGCACGTTCC AGCTGCTGAT      120

GGAGCACATC AACAGAGATCA CGTCGTACAA CGGCGGTGAC CAGGGGTACC TGAACGAGAT     180

ATTCACATGG TGGCACCGCA TCCCCAAGCA CATGAACTTC CTGAAGCACT TCTGGGAGGG      240

CGACAGCGAG GAGGCCAAGG CGAAGAAGAC CCAGCTGTTT GGCGCCGACC CGCCGAACCT      300

CTATGTGCTT CACTACCTGG GGCCTGAACC ATGGCTGTGC TTCAAGGGAC TATGACTGCA      360

ACTGGGAACA ACTTCAATGG ATGCCTGAAT TCCCAAAGCG ACTCGCGCAC AACCGGGTGG      420

TGGAAAGACG CACGACAAGA TCCCCCGGAA NTCCAATCCC TACTGCCTTC TGAGGACGAN      480

GCAAGAAGGC CGGCCTGGAG TGGGGACCGG AGGCAAGCGG AGAAGGCGAA CCGGGAGGAC      540

GGGCAATGGC GGCGGGACAT CACCGATTCG AGGCTCAAGA ACTGCTTCAA AANTTCGG       598

(2) INFORMATION FOR SEQ ID NO:26:

(i) SEQUENCE CHARACTERISTICS:
        (A) LENGTH: 117 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: wle1n.pk0056.b2

(xi) SEQUENCE DESCRIPTION: SEQ ID NO: 26:

Arg Asn Val Asp Phe Leu Phe Ala Met Pro Glu Ile Thr Ala Thr Gly
1               5                   10                  15

Asn Asn Ala Thr Leu Phe Asn Ser Gly Val Met Val Ile Glu Pro Ser
            20                  25                  30

Asn Cys Thr Phe Gln Leu Leu Met Glu His Ile Asn Glu Ile Thr Ser
        35                  40                  45

Tyr Asn Gly Gly Asp Gln Gly Tyr Leu Asn Glu Ile Phe Thr Trp Trp
    50                  55                  60

His Arg Ile Pro Lys His Met Asn Phe Leu Lys His Phe Trp Glu Gly
65                  70                  75                  80

Asp Ser Glu Glu Ala Lys Ala Lys Thr Gln Leu Phe Gly Ala Asp
                85                  90                  95

Pro Pro Asn Leu Tyr Val Leu His Tyr Leu Gly Pro Glu Pro Trp Leu
            100                 105                 110

Cys Phe Lys Gly Leu
        115